US012230160B2

(12) United States Patent
Masuda et al.

(10) Patent No.: US 12,230,160 B2
(45) Date of Patent: Feb. 18, 2025

(54) EVALUATION MODEL FOR ENDOSCOPIC ENDONASAL SURGERY, SIMULATED DURA MATER UNIT, AND OPERATIVE TECHNIQUE EVALUATION METHOD

(71) Applicant: National University Corporation Tokai National Higher Education and Research System, Aichi (JP)

(72) Inventors: Taisuke Masuda, Nagoya (JP); Fumihito Arai, Nagoya (JP)

(73) Assignee: NATIONAL UNIVERSITY CORPORATION TOKAI NATIONAL HIGHER EDUCATION AND RESEARCH SYSTEM, Aichi (JP)

( * ) Notice: Subject to any disclaimer, the term of this patent is extended or adjusted under 35 U.S.C. 154(b) by 735 days.

(21) Appl. No.: 17/421,953

(22) PCT Filed: Jan. 10, 2019

(86) PCT No.: PCT/JP2019/000507
§ 371 (c)(1),
(2) Date: Jul. 9, 2021

(87) PCT Pub. No.: WO2020/144806
PCT Pub. Date: Jul. 16, 2020

(65) Prior Publication Data
US 2022/0114915 A1    Apr. 14, 2022

(51) Int. Cl.
*G09B 23/30* (2006.01)
*G09B 23/28* (2006.01)

(52) U.S. Cl.
CPC ................................ *G09B 23/285* (2013.01)

(58) Field of Classification Search
CPC ................................ G09B 23/28; G09B 23/30
(Continued)

(56) References Cited

U.S. PATENT DOCUMENTS 3,009,265 A * 11/1961 Bezark ................... G09B 23/34
434/270
4,708,836 A * 11/1987 Gain ....................... G09B 23/30
264/222

(Continued)

FOREIGN PATENT DOCUMENTS

CN    203562128 U    4/2014
CN    105719550 A    6/2016
(Continued)

OTHER PUBLICATIONS

Decision of Rejection dated Nov. 28, 2023 issued in the corresponding Chinese Patent Application No. 201980088675.7, with English machine translation.
(Continued)

*Primary Examiner* — Kurt Fernstrom
(74) *Attorney, Agent, or Firm* — Rimon P.C.

(57) ABSTRACT

The object is to provide an evaluation model that can evaluate how much external force is being applied to a brain organ and/or a cranial bone during an endoscopic endonasal surgery. The object can be achieved by an evaluation model for endoscopic endonasal surgery including: a simulated head part; and a distortion sensor, in which the simulated head part includes a simulated cranium part, the simulated cranium part includes a simulated nasal cavity, and the distortion sensor is arranged in a part of the simulated head part.

19 Claims, 8 Drawing Sheets

(58) Field of Classification Search
USPC .......................................................... 434/270
See application file for complete search history.

(56) References Cited

U.S. PATENT DOCUMENTS

| | | | | |
|---|---|---|---|---|
| 9,504,492 | B2* | 11/2016 | Haberl | A61F 2/30942 |
| 10,181,270 | B1* | 1/2019 | Fuller | G09B 23/30 |
| 11,109,817 | B2* | 9/2021 | Everman | A61B 5/746 |
| 2005/0100873 | A1* | 5/2005 | Meythaler | G09B 23/30 434/267 |
| 2007/0020598 | A1* | 1/2007 | Yamashita | G09B 23/34 434/267 |
| 2011/0165547 | A1* | 7/2011 | Hudson | G09B 23/34 434/270 |
| 2014/0212864 | A1* | 7/2014 | Rios | G09B 23/285 434/270 |
| 2016/0140879 | A1* | 5/2016 | Hananel | G09B 23/30 434/270 |
| 2016/0155364 | A1* | 6/2016 | Piron | G01R 33/58 434/270 |
| 2018/0033339 | A1* | 2/2018 | Kerins | G09B 23/34 |
| 2018/0114466 | A1 | 4/2018 | Ono et al. | |
| 2019/0333414 | A1* | 10/2019 | Nakano | G09B 9/00 |

FOREIGN PATENT DOCUMENTS

| | | |
|---|---|---|
| CN | 106157724 A | 11/2016 |
| CN | 106898221 A | 6/2017 |
| CN | 108257468 A | 7/2018 |
| CN | 108320648 A | 7/2018 |
| CN | 108847108 A | 11/2018 |
| JP | 2001-005377 A | 1/2001 |
| JP | 2004-347623 A | 12/2004 |
| JP | 2004-348095 A | 12/2004 |
| JP | 2016-180962 A | 10/2016 |
| JP | 2017-074296 A | 4/2017 |

OTHER PUBLICATIONS

International Search Report and Written Opinion of Internatonal Patent Application No. PCT/JP2019/000507, mailed Apr. 2, 2019; with partial English translation.
Notice of Reasons for Refusal issued in corresponding Japanese Patent Application No. 2020-565103, dated Feb. 22, 2021; with English translation.
Okuda Takeshi, "Development of Training System for Nasal Endoscopic Surgery," Currently Practical Neurosurgery, 2013, vol. 23, No. 3, pp. 331-336; cited in the International Search Report and Written Opinion.
Office Action issued in the corresponding Chinese Application No. 201980088675.7 dated Sep. 2, 2022, with English Translation.
Second Office Action issued in the corresponding Chinese Application No. 201980088675.7 dated Jun. 30, 2023, with English Translation.
Reexamination Notice dated Aug. 12, 2024 issued in the corresponding Chinese Patent Application No. 201980088675.7, with English machine translation.
Review of the Decision dated Oct. 18, 2024 issued in the corresponding Chinese Patent Application No. 201980088675.7, with English translation.

* cited by examiner

EVALUATION MODEL FOR ENDOSCOPIC ENDONASAL SURGERY, SIMULATED DURA MATER UNIT, AND OPERATIVE TECHNIQUE EVALUATION METHOD

CROSS-REFERENCE OF RELATED APPLICATIONS

This application is the U.S. National Phase under 35 U.S.C. § 371 of International Patent Application No. PCT/JP2019/000507, filed on Jan. 10, 2019, which in turn claims the benefit of Japanese Application No. 2012-269642, filed on Dec. 10, 2012, the entire disclosures of which Applications are incorporated by reference herein.

TECHNICAL FIELD

The present disclosure relates to an evaluation model for endoscopic endonasal surgery, a simulated dura mater unit, and an operative technique evaluation method using the evaluation model.

BACKGROUND ART

Endoscopic endonasal surgery (EES) is surgery performed by inserting an endoscope and a surgical tool from a nostril through a nasal cavity and performing operation while viewing up the bottom of a brain from below, as illustrated in FIG. 1. As surgery to remove a tumor at the bottom of the brain, for example, around a pituitary gland, craniotomy to cut a skin and a cranial bone of a head and proceed through a gap between brain parts to reach a pituitary gland is known, however, which may cause a high patient burden and a risk of damage to brain tissues. On the other hand, endoscopic endonasal surgery does not require incision of the skin or the cranial bone of the head and thus may cause a less patient burden and a less risk of damage to brain tissues. Thus, application thereof is in progress recently not only in removal surgery of a pituitary adenoma but also in removal surgery of a craniopharyngioma or a meningioma of a tuberculum sellae area or the like.

As described above, the endoscopic endonasal surgery causes a less patient burden. In the nasal cavity and around the cranial base, however, there are brain organs such as an internal carotid artery which may significantly affect a life or daily life if excessive surgical external force is applied thereto. Thus, training apparatuses for endoscopic endonasal surgery are known.

As one example of training apparatuses for endoscopic endonasal surgery, an apparatus for training to cope with a case of damage to an internal carotid artery is known (see Patent Literature 1). Further, an anatomical model of a human body is known which has a shape matching the surface or the internal structure of a human body and is formed of a material that is close to the human body in mechanical dynamic properties and which is used for training for skill acquisition, such as diagnosis, surgery, or the like in a nasal cavity using an endoscope (see Patent Literature 2).

CITATION LIST

Patent Literature

Patent Literature 1: Japanese Patent Application Laid-Open 2016-180962

Patent Literature 2: Japanese Patent Application Laid-Open 2001-5377

SUMMARY OF INVENTION

Technical Problem

As described above, the endoscopic endonasal surgery is suitably used as an operative technique to mainly remove a tumor around a pituitary gland. There are brain organs such as an optic nerve or the like in addition to the internal carotid artery described above around the pituitary gland, and a tumor formed in such a brain organ is also removed by using a tumor removal tool such as forceps or the like in general. However, there is no known method (apparatus) for evaluating how much external force is applied to the brain organs in removal of a tumor. Further, there is also no known method (apparatus) for evaluating how much external force is applied to the nasal cavity, the cranial base, or the like during insertion of a surgical tool (a scalpel for dura mater incision, a tumor removal tool, or the like) from the nasal cavity and/or during surgery using the surgical tool. Therefore, there is a problem that, even with the apparatus disclosed in Patent Literatures 1 and 2 described above, it is not possible to evaluate how much external force is being applied to a brain organ and/or a cranial bone such as a nasal cavity or a cranial base during insertion of a surgical tool and/or during surgery.

Further, as an optional additional object, endoscopic endonasal surgery requires incision of a dura mater in approach of an endoscope or a tumor removal tool to a tumor at the bottom of a brain and requires suturing of the dura mater after surgery. For repeated training of an operative technique of endoscopic endonasal surgery, it is desirable that only the part subjected to surgery can be replaced and the remaining parts can be used repeatedly. However, there is no known training apparatus for endoscopic endonasal surgery with a replaceable dura mater part.

The present disclosure has been made to solve the problems described above, and intensive studies have newly found that it can be evaluated how much external force is being applied to a brain organ and/or a cranial bone during surgery by fabricating an evaluation model by using a simulated head part including a simulated cranium part in which a simulated nasal cavity is formed and a distortion sensor arranged in the simulated head part. Further, to achieve the optional additional object, it was newly found that, if a simulated dura mater is attached to a first simulated cranium part forming the simulated cranium part instead of being merely attached to the simulated cranium part, a component can be efficiently replaced, and this can achieve the optional additional object.

That is, the object of the present disclosure is to provide an evaluation model that can evaluate external force applied to a brain organ and/or a cranial bone during an endoscopic endonasal surgery, a simulated dura mater unit that is a replaceable component of the evaluation model, and an operative technique evaluation method using the evaluation model.

Solution to Problem

The present disclosure relates to an evaluation model for endoscopic endonasal surgery, a simulated dura mater unit, and an operative technique evaluation method illustrated below.

(1) An evaluation model for endoscopic endonasal surgery, the evaluation model comprising:
- a simulated head part; and
- a distortion sensor,
- wherein the simulated head part includes a simulated cranium part, and the simulated cranium part includes a simulated nasal cavity, and
- wherein the distortion sensor is arranged in a part of the simulated head part.

(2) The evaluation model according to (1) above, wherein the distortion sensor is arranged in the simulated cranium part.

(3) The evaluation model according to (2) above,
- wherein the distortion sensor is arranged in at least one site selected from:
  - a simulated superior turbinate, a simulated middle turbinate, and a simulated inferior turbinate of the simulated nasal cavity, and
  - a simulated nasal septum, a simulated paranasal sinus, and a simulated cribriform plate of the simulated cranium part.

(4) The evaluation model according to any one of (1) to (3) above,
- wherein the simulated head part includes a simulated brain organ, and
- wherein the distortion sensor is arranged in the simulated brain organ.

(5) The evaluation model according to (4) above, wherein the simulated brain organ is at least one selected from a simulated optic nerve, a simulated internal carotid artery, a simulated basilar artery, a simulated posterior cerebral artery, and a simulated pituitary gland.

(6) The evaluation model according to (4) or (5) above, further comprising a simulated tumor.

(7) The evaluation model according to (6) above, wherein the simulated tumor is attached to at least one site selected from the simulated optic nerve and the simulated pituitary gland.

(8) The evaluation model according to any one of (1) to (7) above,
- wherein the simulated cranium part includes
- a first simulated cranium part, and
- a second simulated cranium part,
- wherein the first simulated cranium part forms at least a part of a simulated cranial base, and
- wherein the first simulated cranium part and the second simulated cranium part are formed in an attachable and detachable manner.

(9) The evaluation model according to (8) above, wherein a simulated dura mater is attached to the first simulated cranium part.

(10) The evaluation model according to (8) or (9) above,
- wherein fitting parts for fitting the first simulated cranium part and the second simulated cranium part to each other are formed to the first simulated cranium part and the second simulated cranium part, and
- wherein inner surfaces of the first simulated cranium part and the second simulated cranium part form a continuous surface when the first simulated cranium part and the second simulated cranium part are fitted to each other.

(11) The evaluation model according to any one of (1) to (10) above, further comprising a measuring unit that measures a signal from the distortion sensor.

(12) A simulated dura mater unit used for an evaluation model for endoscopic endonasal surgery,
- wherein the simulated dura mater unit is attached to a first surface of a first simulated cranium part, and
- wherein the first simulated cranium part is configured to form a simulated cranium part of an evaluation model for endoscopic endonasal surgery by being fitted to a second simulated cranium part.

(13) An operative technique evaluation method using an evaluation model for endoscopic endonasal surgery,
- wherein the evaluation model includes at least
- a simulated head part,
- a distortion sensor, and
- a measuring unit that measures a signal from the distortion sensor,
- wherein the simulated head part includes a simulated cranium part, and the simulated cranium part includes a simulated nasal cavity, and
- wherein the distortion sensor is arranged in at least a part of the simulated cranium part through which a surgical tool passes,
- the operative technique evaluation method comprising:
  - a surgical tool insertion step of inserting the surgical tool in a simulated cranium part via the simulated nasal cavity and/or a surgical tool manipulation step of manipulating the surgical tool inside the simulated cranium part;
  - a distortion sensor measurement step of measuring the number of times that the surgical tool comes into contact with the distortion sensor arranged in the simulated cranium part and/or force with which the surgical tool comes into contact with the simulated cranium part in the surgical tool insertion step and/or the surgical tool manipulation step; and
  - an operative technique evaluation step of evaluating the surgical tool insertion step and/or the surgical tool manipulation step from a measurement result of the distortion sensor measurement step.

(14) An operative technique evaluation method using an evaluation model for endoscopic endonasal surgery,
- wherein the evaluation model includes
- a simulated head part,
- a distortion sensor,
- a measuring unit that measures a signal from the distortion sensor, and
- a simulated tumor,
- wherein the simulated head part includes
- a simulated cranium part, and
- a simulated brain organ,
- wherein the simulated cranium part includes a simulated nasal cavity,
- wherein the distortion sensor is arranged in the simulated brain organ, and
- wherein the simulated tumor is attached to the simulated brain organ,
- the operative technique evaluation method comprising:
  - a tumor removal tool approach step of operating a tumor removal tool to approach the simulated tumor via the simulated nasal cavity;
  - a simulated tumor removal step of removing the simulated tumor by the tumor removal tool;
  - a distortion sensor measurement step of measuring external force applied to the distortion sensor arranged in the simulated brain organ in the simulated tumor removal step; and
  - an operative technique evaluation step of evaluating the simulated tumor removal step from a measurement result of the distortion sensor measurement step.

Advantageous Effects

The evaluation model for endoscopic endonasal surgery disclosed in the present application enables evaluation of an operative technique. Further, as an optional additional advantageous effect, because the simulated dura mater is attached to the first simulated cranium part to form a unit, it is possible to easily replace only a part subjected to surgery.

BRIEF DESCRIPTION OF DRAWINGS

FIG. 4 includes diagrams illustrating an overview of other examples of the embodiment of the evaluation model.

FIG. 5 includes diagrams illustrating other examples of the general embodiment of the evaluation model. FIG. 5A illustrates an example in which the evaluation model is arranged in a simulated head frame 8 fabricated with a resin or the like. FIG. 5B illustrates an example in which the evaluation model is covered with a simulated face 9 fabricated with silicon or the like.

FIG. 9 includes photographs illustrating an overview of an operative technique evaluation method of Example 3.

FIG. 10 illustrates a response signal of a distortion sensor obtained by an operative technique evaluation method of Example 3.

DESCRIPTION OF EMBODIMENTS

Figure 1:
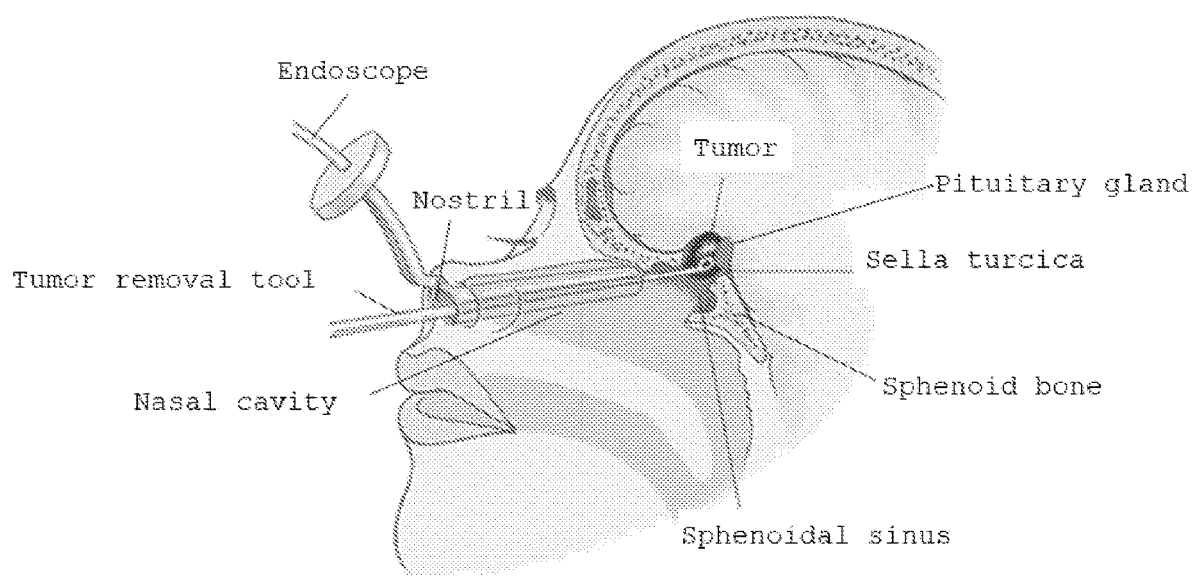
FIG. 1 is a diagram illustrating an overview of endoscopic endonasal surgery.

Each embodiment of an evaluation model for endoscopic endonasal surgery (hereafter, which may be simply referred to as "evaluation model"), a simulated dura mater unit, and an operative technique evaluation method will be described below in detail with reference to the drawings. Note that, in the present specification, members having the same type of functions are labeled with the same or similar reference numerals. Further, duplicated description of the members labeled with the same or similar reference numerals may be omitted.

First Embodiment of Evaluation Model

Figure 2:
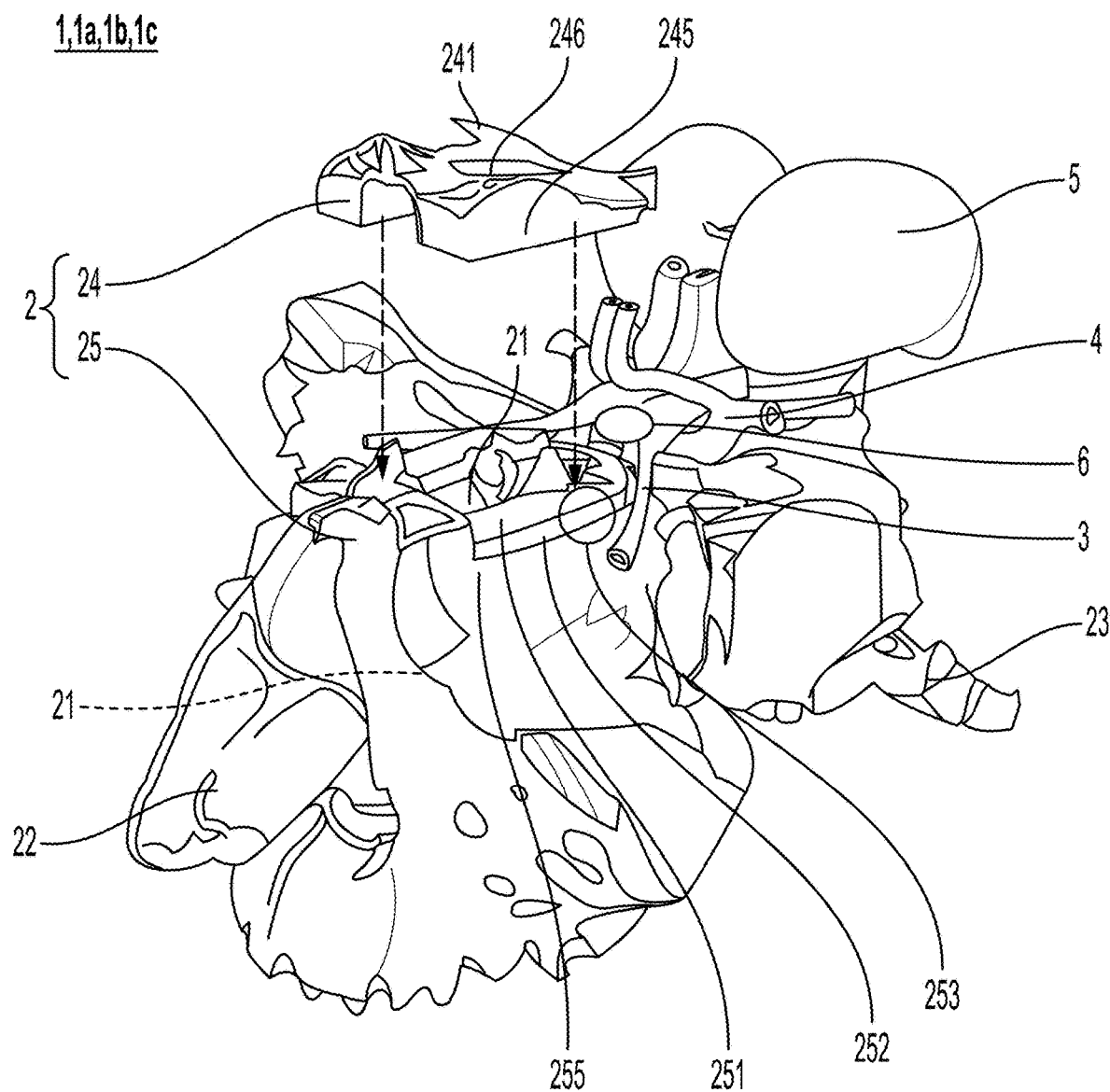
FIG. 2 is a diagram illustrating an overview of an example of an embodiment of an evaluation model.

An evaluation model 1a in a first embodiment will be described with reference to FIG. 2. FIG. 2 is a diagram illustrating an overview of the evaluation model 1a. The evaluation model 1a in the first embodiment includes a simulated head and a distortion sensor (not illustrated). The simulated head includes at least a simulated cranium part 2 and may include a simulated brain organ, if necessary. Note that, in the present specification, "brain organ" means an organ included in a human head except for a cranial bone, and an expression of "includes a simulated brain organ" means any of including only some of the simulated brain organs corresponding to the brain organs or including all of the simulated brain organs corresponding to the brain organs. FIG. 2 illustrates an example including a simulated optic nerve 3, a simulated internal carotid artery 4, and a simulated brain stem 5 as the simulated brain organs. Although not illustrated in FIG. 2 as an example, another simulated brain organ corresponding to a brain organ, such as a simulated cerebrum or a simulated cerebellum, for example, may of course be included. The evaluation model 1a may include a simulated tumor 6, if necessary. Note that, in the present specification, also when an actual human body organ is described, such description may be provided by using the same reference numeral as that of a simulated organ of the evaluation model 1a for the purpose of illustration. When an actual human body organ is described, however, the term "simulated" is not used.

Before respective components of the evaluation model 1a are described in detail, the actual endoscopic endonasal surgery will be described with reference to FIG. 1 and FIG. 2. In the present specification, "endoscopic endonasal surgery" means an operative technique to insert an endoscope or a surgical tool from a nostril and remove the tumor 6 at the bottom of the brain via a nasal cavity (a cavity inside the simulated cranium part 2 at the end of dotted line of the reference numeral 21 in FIG. 2). The endoscopic endonasal surgery is subdivided in accordance with the position of a tumor at the bottom of the brain, in other words, a place where an endoscope and a surgical tool such as a tumor removal tool are routed after routed via the nasal cavity. For example, FIG. 1 illustrates an example of "transsphenoidal surgery" to approach a tumor around a pituitary gland via a nasal cavity and then via a sphenoidal sinus and remove the tumor. Other examples may be:

anterior cranial base surgery to approach a tumor (mainly a tuberculum sellae meningioma tumor) via a nasal cavity and then via an ethmoidal sinus and remove the tumor, clivus backward surgery to approach a tumor behind a clivus via a nasal cavity and then via a sphenoidal sinus and remove the tumor, pyramidal surgery to approach a tumor in the front part of a pyramid via a nasal cavity and then via a maxillary sinus and remove the tumor.

Note that the above examples are typical surgery of the endoscopic endonasal surgery, and surgery of a place other than the above may be employed as long as an endoscope and a surgical tool can be inserted therein via a nasal cavity.

In the actual endoscopic endonasal surgery, for example, transsphenoidal surgery, to cause an endoscope and a surgical tool such as a tumor removal tool to reach a sphenoidal sinus, it is necessary to cut and remove an anterior wall of the sphenoid sinus that is a bone behind the nose. Further, after reaching the sphenoidal sinus, the bottom of a bone including a pituitary gland called sella turcica appears, and it is necessary to drill this out. Further, after drilling the sella turcica, a dura mater appears behind the drilled sella turcica, and by incising the dura mater, it is possible to cause the surgery tool such as the tumor removal tool to reach the tumor 6 around the pituitary gland. Therefore, when the evaluation model 1a is used to faithfully reproduce the actual endoscopic endonasal surgery, it is desirable that a simulated skeleton, organ, and the like that are substantially the same as those of the actual human body be formed for at least a simulated nasal cavity 21 formed in the simulated cranium part 2 and, further, the periphery of a place such as a simulated ethmoidal sinus or a simulated sphenoidal sinus in the deeper where the endoscope or the surgical tool such as the tumor removal tool is routed. On the other hand, when evaluating an operative technique by measuring external force applied to the simulated cranium part such as a simulated nasal cavity or a simulated cranial base when the evaluation model 1a is used to insert the endoscope or the surgical tool such as the tumor removal tool, it is neither necessary to drill the simulated cranium part nor to incise the simulated dura mater. Further, it is not necessary to remove the simulated tumor attached to the simulated brain organ. That is, it is neither necessary to form a simulated dura mater and a bone to be drilled in surgery of a simulated sella turcica or the like nor to form a simulated brain organ or a simulated tumor in the evaluation model 1a. Therefore, in the present specification, "simulated head part" means a member including the simulated cranium part 2 in which "simulated nasal cavity" that is a space in which an endoscope and a surgical tool are inserted is formed. The simulated cranium part 2 may be formed so as to have the same shape as the cranial bone of a human body by forming a cavity of a nasal cavity, a paranasal sinus, or the like, or the like or may be partially different from the cranial bone of a human body. Further, with respect to "simulated nasal cavity", a nasal cavity of a human body may be faithfully simulated or may be partially omitted or deformed as long as an endoscope and a surgical tool can be inserted. The surgical tool is not particularly limited as long as it is a tool used for endoscopic endonasal surgery. For example, the surgical tool may be, for example, a tool such as a cupped forceps, a dismounting forceps to pinch a tissue such as a tumor (hereafter, which may be collectively referred to as "tumor removal tool"), a dura mater incision scalpel, a bone cutting drill, a needle holder used for holding a suture needle for a dura mater, micro shears (scissors), a raspatory (tweezers), a trocar used for guiding the above various tools or the endoscope, or the like.

The simulated cranium part 2 is a member corresponding to a cranial bone of a human body and thus may be formed of a material having a predetermined hardness, for example, a resin or the like. The simulated cranium part 2 can be fabricated by cutting process or 3D printer molding. Further, the simulated cranium part 2 may be molded as a single member or may be divided into two or more parts as illustrated in FIG. 2. FIG. 2 illustrates an example in which the simulated cranium part 2 is formed of a first simulated cranium part 24 and a second simulated cranium part 25. An embodiment in which the simulated cranium part 2 is formed of the first simulated cranium part 24 and the second simulated cranium part 25 in a divided manner will be described later.

Figure 3:
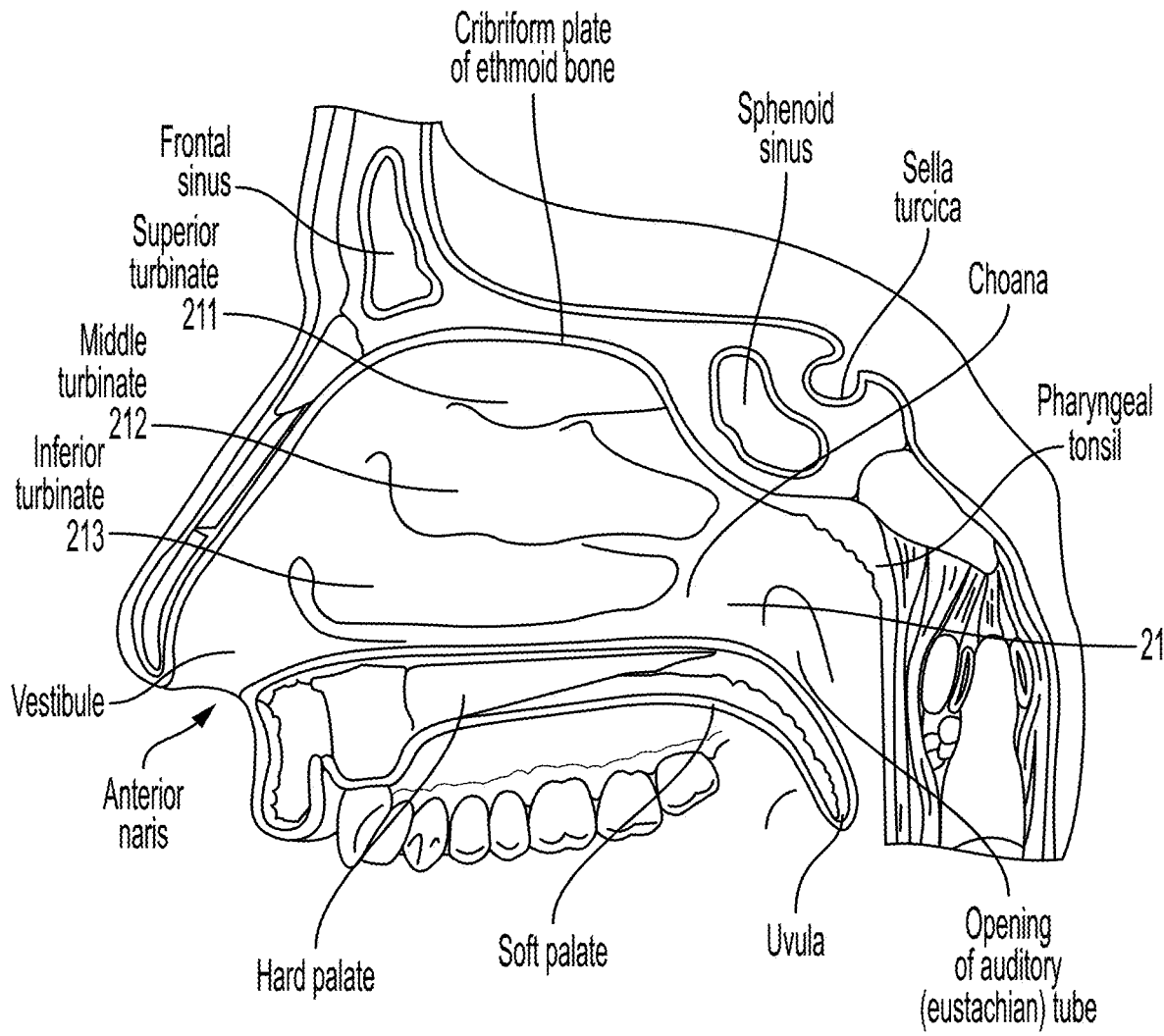
FIG. 3 is a diagram illustrating an example of a place where a distortion sensor is arranged.

The distortion sensor is arranged in a part of the simulated cranium part 2, more specifically, in a place with which the endoscope or the surgery tool easily come into contact when passing through the place and/or a place to which external force is likely to be applied by manipulation of the surgery tool during surgery. FIG. 3 is a diagram illustrating an example of a place where the distortion sensor is arranged, and the place may be, for example, a superior turbinate 211, a middle turbinate 212, an inferior turbinate 213, or the like protruding inside the nasal cavity 21 from the outer wall of the nasal cavity 21 of a human body. Further, as illustrated in FIG. 2, the distortion sensor may be formed in a simulated nasal septum 22 laterally dividing the simulated nasal cavity 21. In addition, although not illustrated, the position of the distortion sensor may be the inner wall of a paranasal sinus such as an ethmoidal sinus, a maxillary sinus, a sphenoidal sinus, or the like or a position corresponding to a cribriform plate or the like of the center of an ethmoid bone of the simulated cranium part 2.

The distortion sensor is not particularly limited as long as it can detect external force applied to the simulated cranium part 2 and may be, for example, a linearly formed piezoelectric element, an optical fiber, a thin film distortion sensor of Cr—N or the like, a liquid pressure sensor or an air pressure sensor, or the like. A commercial product can be used for each of the distortion sensors described above.

With respect to a specific using method of the distortion sensor, for example, when the place of the simulated cranium part 2 where the distortion sensor is arranged is formed in a hollow shape, a linearly formed piezoelectric element or an optical fiber can be inserted in the hollow. Note that, when a linearly formed piezoelectric element or an optical fiber is inserted in the simulated cranium part 2 formed in a hollow shape, if a gap is present between the wall surface of the hollow of the simulated cranium part 2 and the linear piezoelectric element or the optical fiber, the number of times or the force of contact made by the surgical tool may be unable to be accurately detected. Thus, if there is a difference between the size of the hollow formed in the simulated cranium part 2 and the size of the linear piezoelectric element or the optical fiber to be inserted, a material such as a gel may be filled in the gap between the wall surface of the hollow of the simulated cranium part 2 and the linear piezoelectric element or the optical fiber, if necessary.

Further, as an example other than the case where a hollow is formed in the simulated cranium part 2, a liquid pressure sensor (or an air pressure sensor) may be arranged in the hollow of the simulated cranium part 2, furthermore, a liquid (or a gas) may be filled in the hollow, and the hollow may then be sealed.

Further, when the simulated cranium part 2 is formed in a solid shape, a thin film distortion sensor may be attached to the surface of the simulated cranium part 2.

The distortion sensor arranged in the simulated cranium part 2 can be connected to a measuring unit by using an electric wire or the like, and a signal of the distortion sensor can be transmitted to the measuring unit. The measuring unit can be suitably selected in accordance with the type of the distortion sensor to be used.

With the use of the evaluation model 1a according to the first embodiment, it is possible to evaluate external force applied to the cranium part 2 in an endoscopic endonasal surgery.

Second Embodiment of Evaluation Model

An evaluation model 1b in a second embodiment will be described with reference to FIG. 2. In the second embodiment, features different from those of the first embodiment will be mainly described, and duplicated description for the features already described in the first embodiment will be omitted. Thus, needless to say, the feature already described in the first embodiment can also be employed in the second embodiment even when not explicitly described in the second embodiment.

The evaluation model 1b of the second embodiment differs from the evaluation model 1a of the first embodiment in that the evaluation model 1b includes the simulated cranium part 2 and a simulated brain organ and that the distortion sensor is arranged in the simulated brain organ instead of the simulated cranium part 2. The evaluation model 1b according to the second embodiment is used for evaluating external force applied to a brain organ in an endoscopic endonasal surgery. Therefore, the brain organ to which the distortion sensor is provided may be, for example, the optic nerve 3 where the tumor 6 is likely to occur or a nerve, an artery, or the like where a serious situation may occur when damaged by external force of a surgery tool such as a tumor removal tool during surgery. The nerve may be, for example, an optic nerve, an oculomotor nerve, a pulley nerve, a trigeminal nerve, an ophthalmic nerve, a maxillary nerve, an abducens nerve, or the like. Further, the artery may be, for example, an internal carotid artery, an anterior cerebral artery, a middle cerebral artery, a basilar artery, a posterior cerebral artery, a vertebral artery, a superior cerebellar artery, an anterior inferior cerebellar artery, a posterior communicating artery, an anterior communicating artery, or the like. Note that the nerves and the arteries listed above are mere examples, and the distortion sensor may be arranged in simulated brain organs corresponding to other brain organs. In the following, an example in which the distortion sensor is arranged in the simulated optic nerve 3 will be described.

The simulated optic nerve 3 is a member corresponding to an optic nerve of a human body and can thus be fabricated by 3D printer molding using a relatively flexible resin material. Note that, since the distortion sensor described later is arranged in the simulated optic nerve 3, the simulated optic nerve 3 can be formed in a hollow shape or a solid shape in accordance with the distortion sensor to be used. Further, the simulated optic nerve 3 may be fabricated separately from the simulated cranium part 2 or may be integrally molded by using a 3D printer. For example, it is possible to adjust a desired site such as the simulated cranium part 2 or the simulated optic nerve 3 to have a desired hardness by using materials of different hardness as molding resins for the 3D printer and molding the materials while changing the combination ratio of the materials.

The distortion sensor is used for detecting how much external force is being applied to the simulated optic nerve 3 when the tumor removal tool is used to remove the simulated tumor 6 after the simulated tumor 6 is attached to the simulated optic nerve 3. The distortion sensor is not particularly limited as long as it can detect force applied to the simulated optic nerve 3, and the same distortion sensor illustrated as the example in the first embodiment can be used.

With respect to a specific using method of the distortion sensor, for example, when the simulated optic nerve 3 is formed in a hollow shape, a linearly formed piezoelectric element or an optical fiber can be inserted in the hollow.

Note that, when a linear piezoelectric element or an optical fiber is inserted in the simulated optic nerve 3 formed in a hollow shape, if a gap is present between the wall surface of the hollow of the simulated optic nerve 3 and the linear piezoelectric element or the optical fiber, force applied when the simulated tumor 6 is pulled and separated may be unable to be accurately detected. Thus, if there is a difference between the size of the hollow formed in the simulated optic nerve 3 and the size of the linear piezoelectric element or the optical fiber to be inserted, a material such as a gel may be filled in the gap between the wall surface of the hollow of the simulated optic nerve 3 and the linear piezoelectric element or the optical fiber, if necessary.

Further, as an example other than the case where the simulated optic nerve 3 is formed in a hollow shape, a liquid pressure sensor (or an air pressure sensor) may be arranged in the hollow of the simulated optic nerve 3, furthermore, a liquid (or a gas) may be filled in the hollow, and the hollow may then be sealed.

Further, when the simulated optic nerve 3 is formed in a solid shape, a thin film distortion sensor may be attached to the surface of the simulated optic nerve 3.

The distortion sensor may be provided to the whole simulated optic nerve 3 or may be provided to a part of the simulated optic nerve 3. When the distortion sensor is provided to a part of the simulated optic nerve 3, the distortion sensor and the measuring unit can be connected by an electric wire or the like, and a signal of the distortion sensor can be transmitted to the measuring unit. The measuring unit can be suitably selected in accordance with the type of the distortion sensor to be used. Further, when the distortion sensor is provided to a part of the simulated optic nerve 3, the distortion sensor can be provided to a place to which the simulated tumor 6 described later is attached. More specifically, when a linearly formed piezoelectric element, an optical fiber, or a thin film distortion sensor is used as the distortion sensor, these distortion sensors can be provided to the place to which the simulated tumor 6 is attached. Further, when a liquid pressure sensor (or an air pressure sensor) is used as the distortion sensor, at least the place of the simulated optic nerve 3 to which the simulated tumor 6 is attached is formed in a hollow shape, a liquid (or a gas) can be filled therein, and the liquid pressure sensor (or the air pressure sensor) can be arranged in the position in contact with the liquid (or the gas).

The material of the simulated tumor 6 is not particularly limited as long as it has a hardness close to the hardness of an actual tumor, can be adhered to the simulated optic nerve 3, and can be removed (pulled and separated) from the simulated optic nerve 3 by using a tumor removal tool. For example, a urethane gel, a silicon rubber, a biological origin hydrogel (collagen, gelatin, or the like), or the like may be used. Note that, while the simulated tumor 6 may be originally attached to the simulated optic nerve 3 as a component of the evaluation model 1b, the simulated tumor 6 is not required to be included in the component of the evaluation model 1b, and the user may separately prepare a material for the simulated tumor 6 and attach the material to the simulated optic nerve 3 when using the evaluation model 1b. Alternatively, the simulated tumor 6 enclosed in a tube or the like may be provided in combination with the evaluation model 1b as a kit.

The place to which the simulated tumor 6 is attached is not particularly limited as long as it is a place where a tumor actually occurs and the operative technique is intended to evaluate. For example, the place where a tumor is relatively more likely to occur in the optic nerve 3 may be the optic chiasma at which the optic nerves 3 from both eyes intersect.

Note that, although the above example has been described mainly for the optic nerve 3, a tumor is relatively more likely to occur also in the tuberculum sellae area or the clivus area at the bottom of the brain. A tumor that has occurred in the tuberculum sellae area entangles from the inside to the periphery of the internal carotid artery 4, and the tumor 6 infiltrates the optic nerve 3. Therefore, the simulated internal carotid artery 4 may be further provided as a simulated brain organ, and the distortion sensor may be arranged in the simulated optic nerve 3 and the simulated internal carotid artery 4. Alternatively, the distortion sensor may be arranged only in the simulated internal carotid artery 4. The simulated internal carotid artery 4 can be fabricated in the same process as the simulated optic nerve 3, and the distortion sensor can also be arranged in the same process as for the simulated optic nerve 3. The fabrication can be performed in the same process also when the distortion sensor is arranged in a simulated brain organ other than the simulated optic nerve 3 and the simulated internal carotid artery 4.

Further, another place where the tumor 6 is likely to occur may be the clivus area. In such a case, a basilar artery or a posterior cerebral artery is provided as simulated brain organs, and the distortion sensor can be arranged in the basilar artery or the posterior cerebral artery. The formation of the basilar artery or the posterior cerebral artery and the arrangement of the distortion sensor to the basilar artery or the posterior cerebral artery can be performed in the same manner as for the simulated optic nerve 3.

Note that the above example has been described mainly for the example of a case where the tumor 6 attached to a brain organ is removed. On the other hand, when using the evaluation model 1b to measure only external force applied to a brain organ due to manipulation of a surgical tool such as a tumor removal tool, the attachment of the simulated tumor 6 to the simulated brain organ is not essential. In other words, in the evaluation model 1b, any simulated brain organ for which measurement of the impact of external force due to manipulation of a surgical tool is desired in an endoscopic endonasal surgery can be provided, and the distortion sensor can be arranged in the simulated brain organ.

As described above, with the use of the evaluation model 1b according to the second embodiment, it is possible to evaluate external force applied to a brain organ in an endoscopic endonasal surgery.

Third Embodiment of Evaluation Model

Figure 4B:
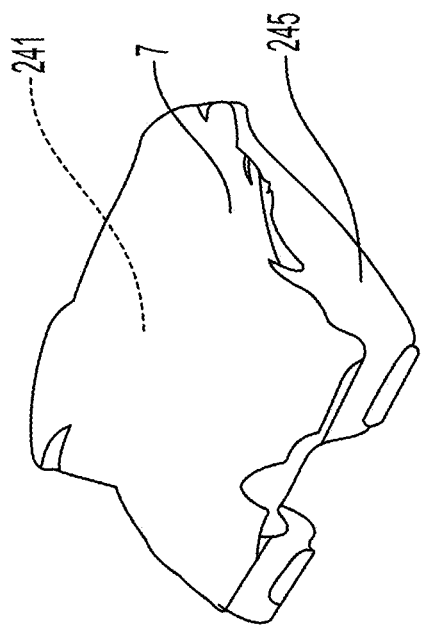
FIG. 4B is an enlarged view of the first simulated cranium part 24 when viewed from a first surface 241 side of the first simulated cranium part 24.
Figure 4C:
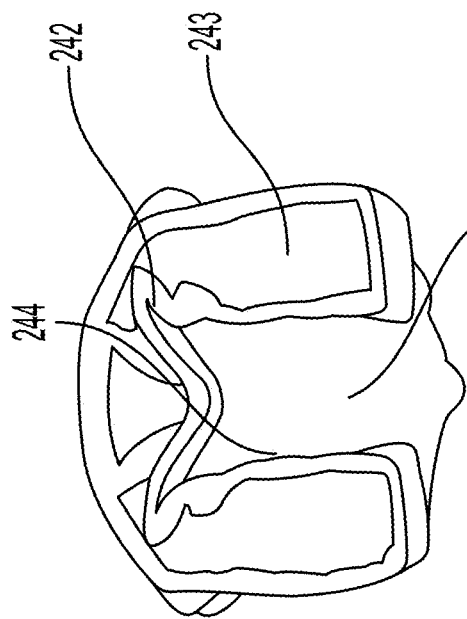
FIG. 4C is an enlarged view of the first simulated cranium part 24 when viewed from a second surface 242 side of the first simulated cranium part 24.
Figure 4A:
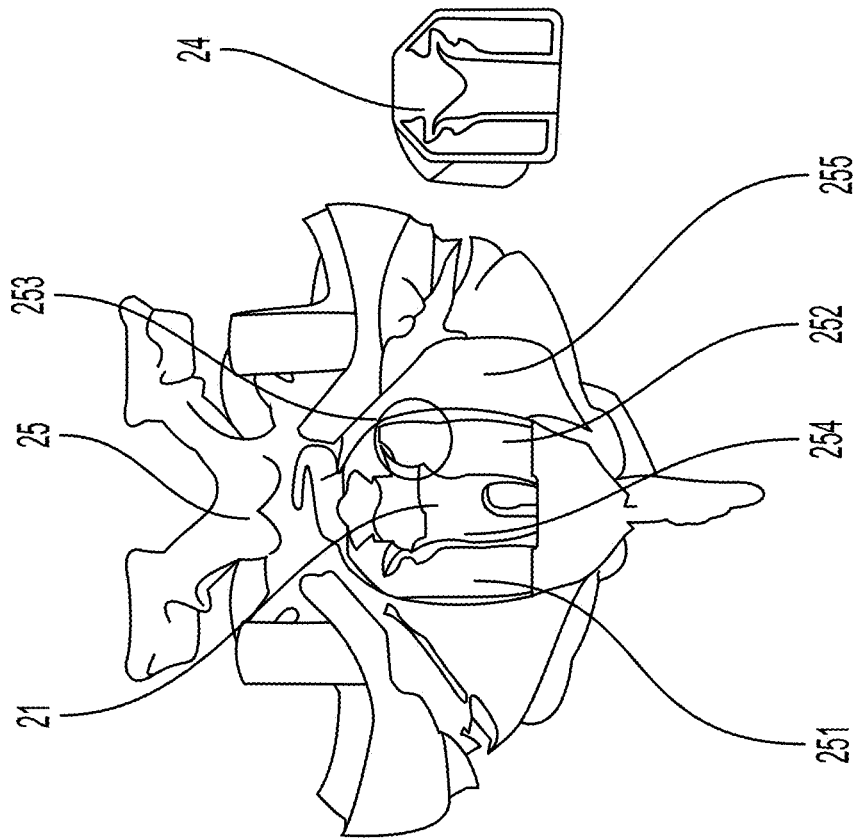
FIG. 4A is a diagram illustrating a state where a first simulated cranium part 24 and a second simulated cranium part 25 of the evaluation model are separated from each other.

An evaluation model 1c in a third embodiment will be described with reference to FIG. 2 and FIG. 4. FIG. 4A is a diagram illustrating a state where the first simulated cranium part 24 and the second simulated cranium part 25 of the evaluation model 1c are separated from each other, FIG. 4B is an enlarged view of the first simulated cranium part 24, which is a diagram viewed from the first surface 241 side of the first simulated cranium part 24, and FIG. 4C is an enlarged view of the first simulated cranium part 24, which is a diagram viewed from the second surface 242 side of the first simulated cranium part 24. In the third embodiment, features different from those of the first and second embodiments will be mainly described, and duplicated description for the features already described in the first and second embodiments will be omitted. Thus, needless to say, the feature already described in the first and second embodiments can also be employed in the third embodiment even when not explicitly described in the third embodiment.

The evaluation model 1c of the third embodiment differs from those of the first and second embodiments in that the simulated cranium part 2 is divided into the first simulated cranium part 24 and the second simulated cranium part 25 and fitting parts for fitting the first simulated cranium part 24 and the second simulated cranium part 25 to each other are formed in the first simulated cranium part 24 and the second simulated cranium part 25. In the example illustrated in FIG. 2 and FIG. 4, (1) the second simulated cranium part 25 has a third surface 251 in contact with the second surface 242 of the first simulated cranium part 24, a cut-off 252 is formed in the periphery of the third surface 251, and thereby a protrusion 253 is formed (indicated by the circle of FIG. 2 and FIG. 4), (2) a recess 243 fitted to the protrusion 253 of the second simulated cranium part 25 is formed on the second surface 242 side of the first simulated cranium part 24, and thereby (3) the first simulated cranium part 24 and the second simulated cranium part 25 can be fitted in a detachable manner.

The fitting part (the recess 243, the protrusion 253 in the above example) is not limited to the example illustrated in FIG. 2 and FIG. 4 as long as it can fit the first simulated cranium part 24 and the second simulated cranium part 25 to each other. For example, the recess and the protrusion may be formed by members opposite to the example illustrated in FIG. 2 and FIG. 4. Further, instead of the configuration in which the cut-off 252 is formed and thereby the protrusion 253 is formed, any number of one or more protrusions (or recesses) may be formed on the third surface 251, one or more recesses (or protrusions) fitting to the one or more protrusions (or recesses) may be formed in the second surface 242, and thereby the first simulated cranium part 24 and the second simulated cranium part 25 may be fitted to each other.

It is preferable that the inner surfaces of the first simulated cranium part 24 and the second simulated cranium part 25 form a continuous surface when the first simulated cranium part 24 and the second simulated cranium part 25 are fitted to each other. Note that, in the present specification, "inner surface" means the surface on the simulated nasal cavity 21 side of the first simulated cranium part 24 and the second simulated cranium part 25. Further, in the present specification, "continuous surface" means that, when the first simulated cranium part 24 and the second simulated cranium part 25 are fitted to each other, there is no level difference at the connection part between the inner surface (first inner surface 244) of the first simulated cranium part 24 and the inner surface (second inner surface 254) of the second simulated cranium part 25 as if a continuous single surface were formed. If there is a level difference at the connection part of the inner surfaces of the first simulated cranium part 24 and the second simulated cranium part 25, the operator will feel strange because of the difference from the actual human body when using the evaluation model 1c. However, with the connection part being formed of a continuous surface, the operator is able to use the evaluation model 1c with the same feeling as with an actual human body.

Note that the outer surface (the surface opposite to the inner surface) formed when the first simulated cranium part 24 and the second simulated cranium part 25 are fitted to each other is not required to be a continuous surface because the endoscope and the surgery tool are not inserted. On the other hand, in terms of having the surface more similar to an actual human body, the connection part between the outer surface (first outer surface 245) of the first simulated cranium part 24 and the outer surface (second outer surface 255) of the second simulated cranium part 25 may also form a continuous surface in the same manner as with the inner surface.

Note that, although substantially a U-shape hole 246 penetrating the first surface 241 and the second surface 242 is formed in the first simulated cranium part 24 in the example illustrated in FIG. 2 and FIG. 4, the hole 246 may or may not be formed. When the hole 246 is not formed, it is possible to cause an endoscope and a surgical tool to reach the simulated tumor 6 via the simulated nasal cavity 21 without resecting the simulated cranial base or the like before causing the surgical tool such as a tumor removal tool to reach the simulated dura mater 7 (described later in detail), and it is therefore possible to use the evaluation model 1c only for evaluation of the operative technique of a method of removing (separating) the simulated tumor 6. Further, when the hole 246 is formed, it is possible to use the evaluation model 1c in a way closer to actual surgery such as resection of a simulated cranial base. Note that the hole 246 may or may not be provided in the simulated cranium part 2 also in the evaluation models 1a and 1b according to the first and second embodiments.

Note that the first simulated cranium part 24 can also be used as a pedestal to which the simulated dura mater 7 described later is attached. When the first simulated cranium part 24 to which the simulated dura mater 7 is attached is a replacement component, the size thereof is preferably small. Therefore, the first simulated cranium part 24 preferably includes a part of the cranial base in contact with the dura mater 7 in an actual human body. More specifically, when the evaluation model 1c is used for evaluation of an operative technique of removing a tumor around a pituitary gland in accordance with endoscopic endonasal surgery, the first simulated cranium part 24 preferably includes a cranial base portion with which a surgical tool such as a tumor removal tool routed via the simulated nasal cavity 21 can approach a part around the pituitary gland. The range of the cranial base forming the first simulated cranium part 24 can of course be suitably set in accordance with the position of a tumor approached by a surgical tool. Further, the thickness of the first simulated cranium part 24 (the length in the direction of the simulated nasal cavity 21 from the first surface 241 to which the simulated dura mater 7 is attached) can also be suitably adjusted. For example, the first simulated cranium part 24 may be formed of only the part corresponding to the cranial base or may include a part of the simulated nasal cavity 21, a simulated paranasal sinus such as a simulated sphenoidal sinus, or the like.

Fourth Embodiment of Evaluation Model

An evaluation model 1d in a fourth embodiment will be described with reference to FIG. 4. Although the evaluation model 1d in the fourth embodiment differs from the third embodiment in that the simulated dura mater 7 is attached to the first surface 241 of the first simulated cranium part 24, other features are the same as those of the third embodiment. Therefore, in the fourth embodiment, features different from those of the third embodiment will be mainly described, and duplicated description for the features already described in the third embodiment will be omitted. Thus, needless to say, the features already described in the first to third embodiments can also be employed in the fourth embodiment even when not explicitly described in the fourth embodiment.

When the endoscopic endonasal surgery is performed on a human body, it is necessary to incise the dura mater 7 before reaching the tumor 6. After removing the tumor 6, it is then necessary to suture the dura mater 7. Thus, when the evaluation model 1 is used to perform training of incision and suturing of the simulated dura mater 7, it is required to replace the simulated dura mater 7 every time. When actually incising the dura mater 7, the operator will perform incision while pressing an incision tool such as a scalpel against the dura mater 7 from the cranial base side. Thus, when the simulated dura mater 7 is formed in the evaluation model 1, since an incision tool or the like will be pressed against the simulated dura mater 7 from the simulated cranial base side, the simulated dura mater 7 is required to be attached to the simulated cranium part 2 (or the first simulated cranium part 24) with a predetermined peeling strength. If only the simulated dura mater 7 is simply made replaceable, however, it is required for the operator to attach the simulated dura mater 7 to the simulated cranium part 2 (or the first simulated cranium part 24) every time. But, it is difficult to attach the simulated dura mater 7 to the simulated cranium part 2 (or the first simulated cranium part 24), which has a non-planar surface, with the same peeling strength every time On the other hand, the fourth embodiment can achieve significant advantageous effects that, with a simulated dura mater unit in which the simulated dura mater 7 is attached to the first surface 241 of the first simulated cranium part 24 as illustrated in FIG. 4A to FIG. 4C, the operator is able to easily replace the simulated dura mater 7 and maintain the peeling strength constant. Note that, if the fitting parts of the first simulated cranium part 24 and the second simulated cranium part 25 are accurately fabricated, friction force at the fitting parts prevents the first simulated cranium part 24 and the second simulated cranium part 25 from separating even when the simulated dura mater 7 is pushed by an incision tool.

The dura mater 7 is similar to a bird skin. The simulated dura mater 7 is not particularly limited as long as it is fabricated so as to have the structure similar to the dura mater 7, for example, by impregnating a non-woven fabric with an elastic resin material or the like. The raw material used for fabricating the non-woven fabric may be, for example, polyolefin-based polymers such as polyethylene, polypropylene, or the like; polystyrene; polyimide, polyamide, or polyamide-imide; polyarylenes (aromatic polymers) such as poly(para-phenylene oxide), poly(2,6-dimethylphenylene oxide), or poly(para-phenylene sulfide); a material obtained by introducing a sulfonic acid group ($-SO_3H$), a carboxyl group ($-COOH$), a phosphate group, a sulfonium group, an ammonium group, or a pyridinium group in a polyolefin-based polymer, polystyrene, polyimide, or polyarylenes (aromatic polymer); fluorine-containing polymers such as polytetrafluoroethylene, polyvinylidene fluoride, or the like; a perfluorosulfonic acid polymer, a perfluorocarboxylic acid polymer, a perfluorophosphoric acid polymer obtained by introducing a sulfonic acid group, a carboxyl group, a phosphate group in a fluorine-containing polymer framework; a polybutadiene-based compound; a polyurethane-based compound of elastomer, gel, or the like; a silicone-based compound; polyvinyl chloride; polyethylene terephthalate; nylon; polyarylate; or the like. Further, the elastic resin material may be, for example, a rubber material (elastomer) such as a silicone rubber such as polydimethylsiloxane (PDMS), a butadiene rubber, an isoprene rubber, a butyl rubber, a fluorine rubber, an ethylene-propylene rubber, a nitrile rubber, a natural rubber, a polyurethane rubber, a latex rubber, or the like; an emulsion resin; or the like.

Note that it was newly developed by the present inventors that the significant advantageous effect described above can be achieved by using the first simulated cranium part 24 as a pedestal to which the simulated dura mater 7 is attached and providing the first simulated cranium part 24 and the simulated dura mater 7 as an integrated simulated dura mater unit. Therefore, although the simulated dura mater unit is illustrated as a component of the evaluation model 1*d* in the fourth embodiment, the simulated dura mater unit may be provided as a replacement component of the evaluation model 1*d*.

Figures 5A, 5B:
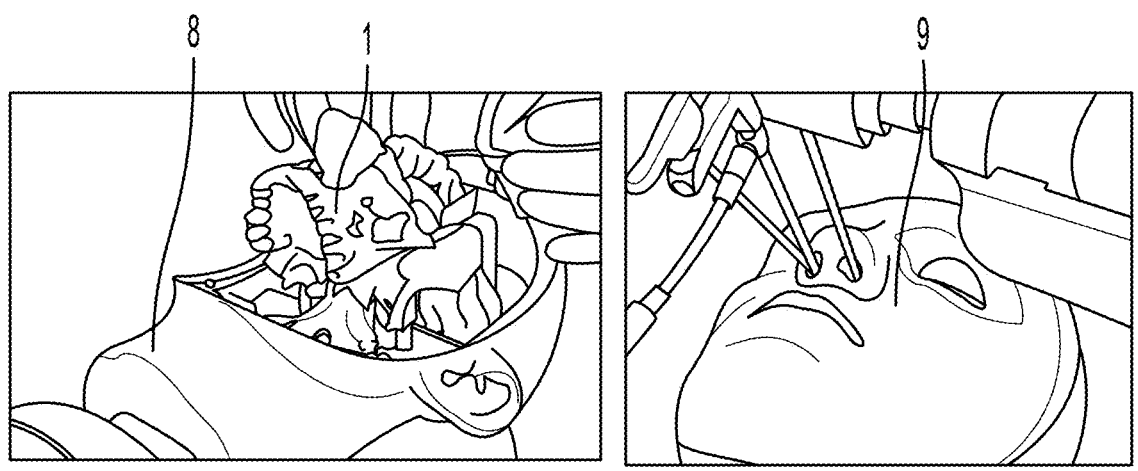

The evaluation devices 1*a* to 1*d* according to the first to fourth embodiments described above are of more specific examples of the embodiments of the evaluation device, and the present invention is not limited to the embodiments described above. Any combination of respective embodiments described above or modification of any component or omission of any component of each embodiment is possible. For example, although the distortion sensor is arranged in the simulated cranium part 2 in the first embodiment and the distortion sensor is arranged in the simulated brain organ in the second embodiment, the distortion sensor may be arranged in both the simulated cranium part 2 and the simulated brain organ. Furthermore, any component may be added to each embodiment described above. For example, as illustrated in FIG. 5A, the evaluation model 1 may be arranged in a simulated head frame 8 fabricated with a resin or the like. Further, as illustrated in FIG. 5B, a simulated face 9 fabricated with silicon or the like may be covered over the evaluation model 1.

First Embodiment of Operative Technique Evaluation Method

Figure 6:
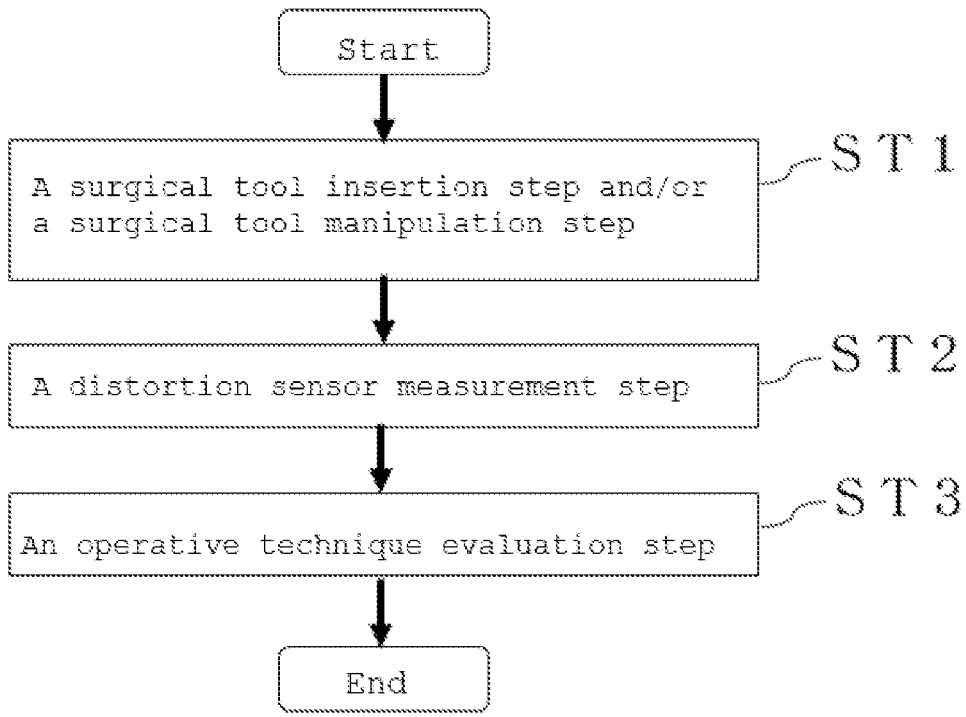
FIG. 6 is a flowchart of a first embodiment of an operative technique evaluation method.

Next, a first embodiment of an operative technique evaluation method will be described with reference to FIG. 6. The first embodiment of an operative technique evaluation method is performed by using at least the simulated cranium part 2, a distortion sensor arranged in the simulated cranium part 2, and a measuring unit. FIG. 6 is a flowchart of the first embodiment of the operative technique evaluation method. The first embodiment of the operative technique evaluation method includes a surgical tool insertion step and/or the surgical tool manipulation step (ST1), a distortion sensor measurement step (ST2), and an operative technique evaluation step (ST3). In the surgical tool insertion step (ST1), a surgical tool is inserted in the simulated cranium part 2 via the simulated nasal cavity 21. Further, in the surgical tool manipulation step (ST1), an operative technique intended to be evaluated during an endoscopic endonasal surgery is performed by using the surgical tool. The operative technique may be, for example, removing a simulated tumor by using a tumor removal tool, cutting a simulated cranium part by using a bone cutting drill, incising a simulated dura mater by using a dura mater incision scalpel, suturing a simulated dura mater by using a needle holder for holding a suture needle for the simulated dura mater, or the like. Note that, in the first embodiment of the operative technique evaluation method, when only the evaluation of an operative technique (manual surgical procedure) to actually manipulate a surgical tool is performed, the surgical tool insertion step is not an essential step. In such a case, a person other than the operator may insert the surgical tool, if necessary. Further, when only the evaluation of the surgical tool insertion step is performed, for example, evaluation of an operative technique using a newly designed surgical tool, in other words, design of a surgical tool for reducing contact in the nasal cavity or the like is performed, the surgical tool manipulation step is not an essential step. In such a case, the operative technique evaluation method also includes an evaluation method for the design of the surgical tool.

In the distortion sensor measurement step (ST2), the number of times that the surgical tool comes into contact with the distortion sensor arranged in the simulated cranium part 2 and/or force with which the surgical tool comes into contact with the simulated cranium part 2 is measured in the surgical tool insertion step and/or the surgical tool manipulation step (ST1). In the operative technique evaluation step (ST3), the surgical tool insertion step and/or the surgical tool manipulation step (ST1) is evaluated from the measurement result of the distortion sensor measurement step (ST2). Note that, in the operative technique evaluation step (ST3), a person may evaluate the operative technique from the result measured in the distortion sensor measurement step (ST2), or an evaluation index such as a cutoff value set in advance based on the measurement value of the distortion sensor may be stored in a computer to cause the computer to make the determination. According to the first embodiment of the operative technique evaluation method, it is possible to evaluate how much external force is being applied to the nasal cavity 21 or the like of a human body and/or what frequency the surgical tool comes into contact with the nasal cavity 21 or the like when the surgical tool is inserted via the simulated nasal cavity 21 and/or the surgical tool is manipulated.

Second Embodiment of Operative Technique Evaluation Method

Figure 7:
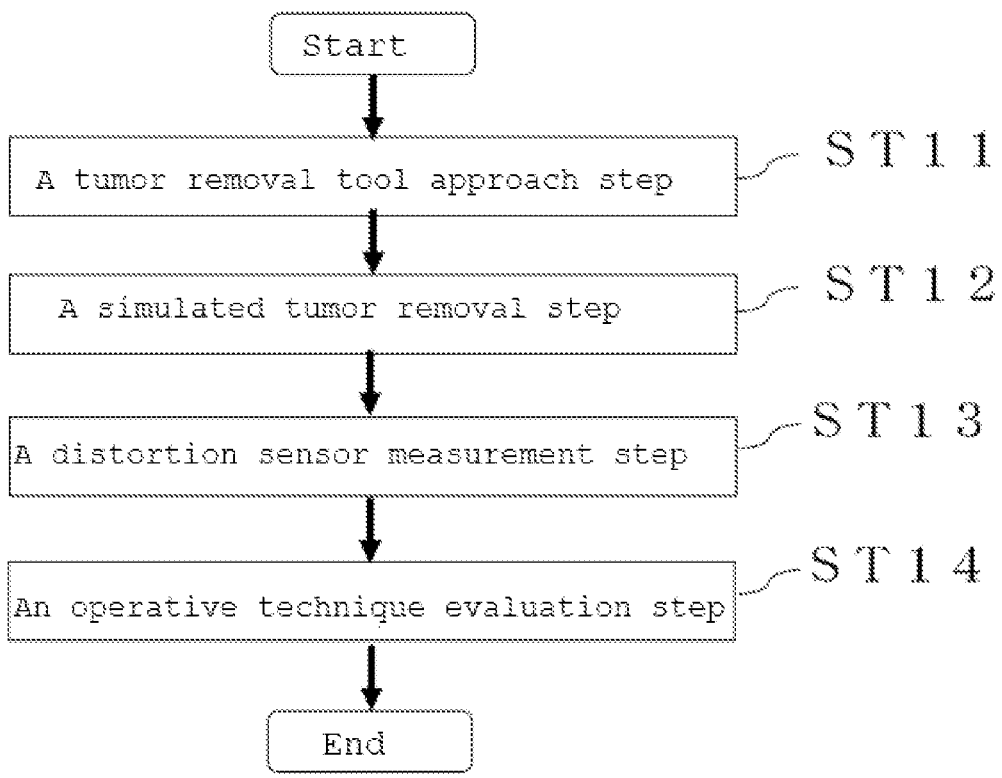
FIG. 7 is a flowchart of a second embodiment of an operative technique evaluation method.

Next, a second embodiment of an operative technique evaluation method will be described with reference to FIG. 7. The second embodiment of an operative technique evaluation method is performed by using the simulated cranium part 2, a simulated brain organ, a distortion sensor arranged in the simulated brain organ, the simulated tumor 6, and a measuring unit. FIG. 7 is a flowchart of the second embodiment of an operative technique evaluation method. The second embodiment of the operative technique evaluation method includes a tumor removal tool approach step (ST11), a simulated tumor removal step (ST12), a distortion sensor measurement step (ST13), and an operative technique evaluation step (ST14). In the tumor removal tool approach step (ST11), a tumor removal tool is operated to approach the simulated tumor 6 via the simulated nasal cavity 21. In the simulated tumor removal step (ST12), the tumor removal tool is used to remove the simulated tumor 6. In the distortion sensor measurement step (ST13), the external force applied to the distortion sensor arranged in the simulated brain organ is measured in the simulated tumor removal step (ST2). In the operative technique evaluation step (ST14), the simulated tumor removal step (ST2) is evaluated from the measurement result of the distortion sensor measurement step (ST3). Note that, in the operative technique evaluation step (ST14), a person may evaluate the operative technique from the result measured in the distortion sensor measurement step (ST13), or an evaluation index such as a cutoff value set in advance based on the measurement value of the distortion sensor may be stored in a computer to cause the computer to make the determination. According to the second embodiment of the operative technique evaluation method, it is possible to evaluate how much external force is being applied to the brain organ such as the optic nerve of the human body when the tumor 6 is removed (separated) by using the tumor removal tool.

Although Examples will be presented below to specifically describe each embodiment, these Examples are merely provided for references to the specific form thereof. These examples are neither to limit nor restrict the scope of the invention.

EXAMPLES

Example 1

[Fabrication of Evaluation Device 1]

Figure 8:
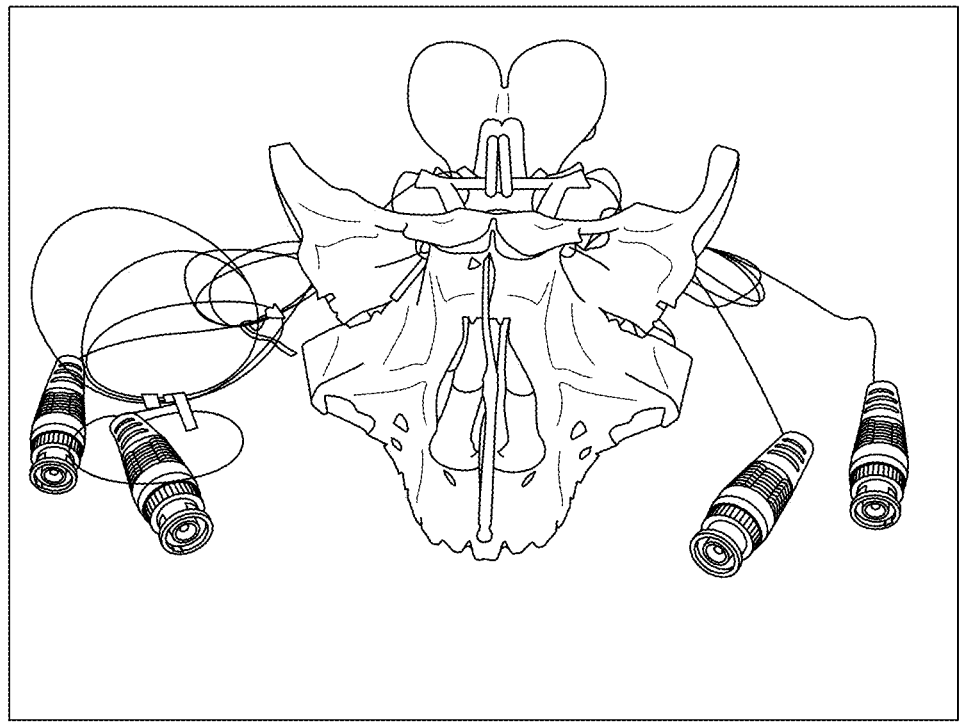
FIG. 8 is a photograph of an evaluation device fabricated in Example 1.

The simulated cranium part 2, the simulated optic nerve 3, the simulated internal carotid artery 4, and the simulated brain stem 5 were integrally molded by using a 3D printer (by 3D systems, Inc., ProJet5500XE). VisiJet CR-WT (by 3D Systems, Inc., ABS-like resin material) and VisiJet CE-NT (by 3D Systems, Inc., rubber-like resin material) were used as molding materials, the portion of the simulated cranium part 2 was fabricated with a high mixing ratio of the ABS-like resin material, and the portions of the simulated optic nerve 3, the simulated internal carotid artery 4, and the simulated brain stem 5 were fabricated with a high mixing ratio of the rubber-like resin material to have flexibility. Next, a linear piezoelectric element (by Mitsui Chemicals, Inc., coaxial line piezoelectric sensor 21110) was used as the distortion sensor, and the distortion sensor was inserted in a hollow of the fabricated hollowed simulated optic nerve 3. Note that, when the distortion sensor was inserted in the hollow of the simulated optic nerve 3, urethane acrylate (by SHIN-NAKAMURA CHEMICAL Co, Ltd., photo-curable monomer material) was used so that no gap occurred between the hollow of the simulated optic nerve 3 and the distortion sensor. Next, the distortion sensor was soldered to a BNC connector to fabricate the evaluation device 1. FIG. 8 is a photograph of the evaluation device fabricated in Example 1. When an evaluation method was performed by using the fabricated device, the device is connected to a measuring instrument (by HIOKI E.E. CORPORATION, data logger) via the BNC connector.

Example 2

[Fabrication of Simulated Dura Mater Unit]

The first simulated cranium part 24 and the second simulated cranium part 25 were fabricated by using the same 3D printer and the same ABS-like resin as those in Example 1. FIG. 4A is a photograph of the second simulated cranium part fabricated in Example 2. Next, a non-woven fabric fabricated with polypropylene was impregnated with an emulsion resin (by Yutaka Make Co., product name: liquid rubber) and dried. Next, another non-woven fabric impregnated with emulsion resin was further overlapped over the dried non-woven fabric impregnated with the emulsion resin and dried, which were repeated to fabricate the simulated dura mater 7 of stacked fabricate non-woven fabrics. Next, the fabricated simulated dura mater 7 was adhered to the first surface 241 of the first simulated cranium part 24 by using an emulsion resin to fabricate a simulated dura mater unit. FIG. 4B and FIG. 4C are photographs of the simulated dura mater unit fabricated in Example 2. Next, the fabricated simulated dura mater unit was covered over the second simulated cranium part 25, and it was confirmed that the fabricated simulated dura mater unit and the second simulated cranium part 25 were firmly fitted to each other and not easily detached. Further, it was confirmed that no level difference was found inside the junction of the fabricated simulated dura mater unit and the second simulated cranium part 25 and thus a continuous surface was formed.

Example 3

[Implementation 1 of Operative Technique Evaluation Method]

Figure 9A:
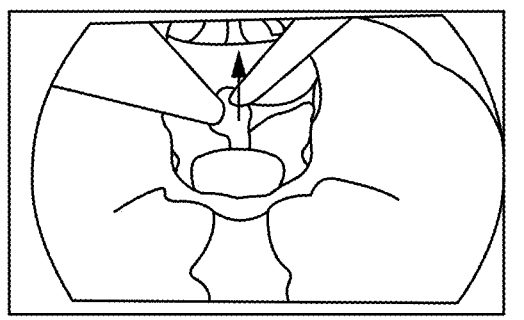
FIG. 9Aa and FIG. 9Ab are photographs illustrating a conventional tumor removal method.
Figure 9A:
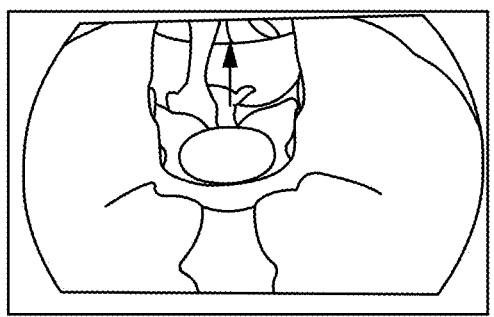
Figure 9B:
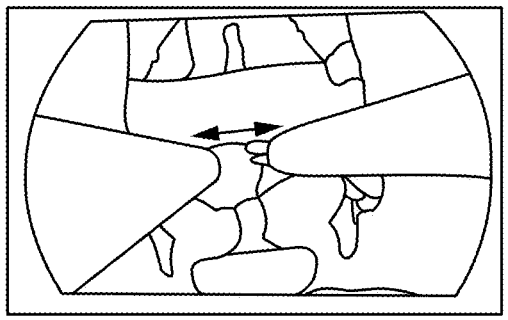
FIG. 9Ba and FIG. 9Bb are photographs illustrating an example of an operative technique different from the conventional technique.
Figure 9B:
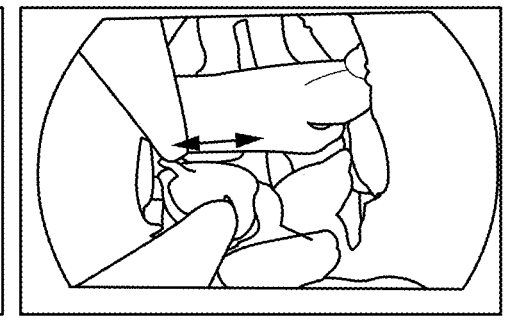

A urethane gel (by EXSEAL Co. Ltd., HO-100) was used for the simulated tumor 6, which was attached to the optic chiasma part of the simulated optic nerve 3 fabricated in Example 1. Next, an endoscope (by Olympus Corporation, EndoArm) and a tumor removal tool (by Fujita Medical Instruments, Co, Ltd., cupped forceps) were inserted via the simulated nasal cavity 21. While the endoscope was used to ensure the field of view, the tumor removal tool was used to remove the simulated tumor 6 by two methods. FIG. 9A is a photograph illustrating a conventional tumor removal method, and the tumor removal tool was used to pinch the simulated tumor 6 (FIG. 9Aa), the tumor removal tool was pulled out (the arrow direction in FIG. 9Aa, 9Ab), and thereby, the tumor was separated from the simulated optic nerve 3 (FIG. 9Ab). On the other hand, FIG. 9B illustrates an example of an operative technique different from the conventional technique, and first, the tumor removal tool was used to separate the simulated tumor 6 attached to the simulated optic nerve 3 while moving the tumor removal tool in the center axis direction of the simulated optic nerve (FIG. 9Ba) and separate the simulated tumor 6 from the simulated optic nerve 3 (FIG. 9Bb), and the tumor removal tool was then used to pinch and remove the simulated tumor 6.

Figure 10A:
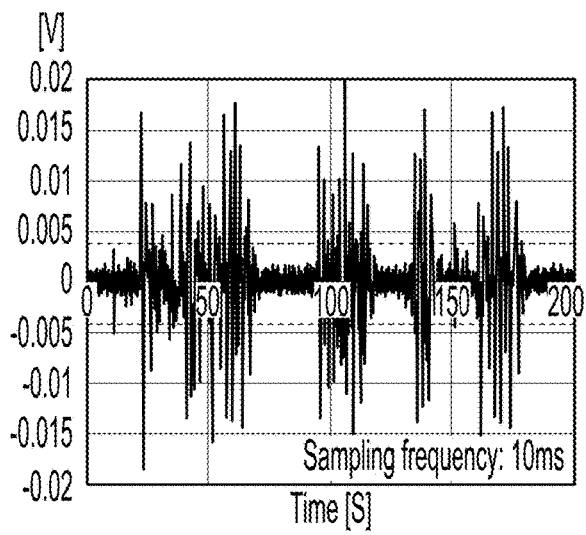
FIG. 10A illustrates a response signal of the distortion sensor when a simulated tumor 6 is removed by the conventional tumor removal method illustrated in FIG. 9A. Further.
Figure 10B:
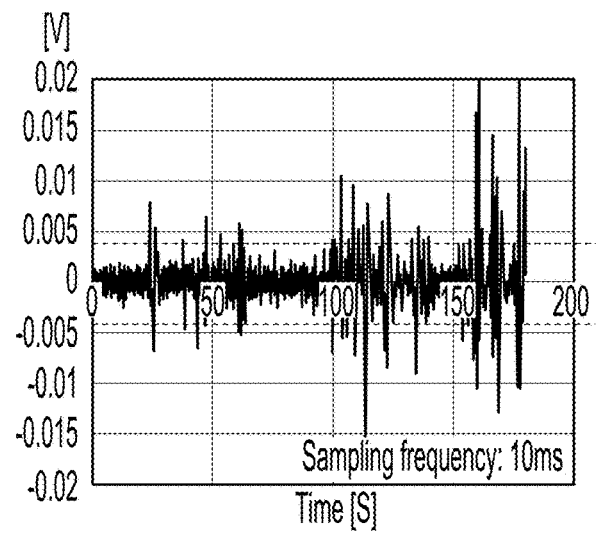
FIG. 10B illustrates a response signal of the distortion sensor when the simulated tumor 6 is removed by the operative technique illustrated in FIG. 9B that is different from the conventional technique.

FIG. 10A illustrates a response signal of the distortion sensor when the simulated tumor 6 was removed by the conventional tumor removal method illustrated in FIG. 9A. Further, FIG. 10B illustrates a response signal of the distortion sensor when the simulated tumor 6 was removed by the operative technique illustrated in FIG. 9B that is different from the conventional technique. It is indicated that, when the signal is more distant from zero on the vertical axis, the force applied to the distortion sensor is larger, in other words, the force applied to the simulated optic nerve 3 is larger when the simulated tumor 6 is removed. As is clear from the response signals in FIG. 10A and FIG. 10B, a difference in operative techniques in removing the simulated tumor 6 made the response signals significantly different. Therefore, the use of the evaluation model disclosed in the present specification enables development and evaluation of an operative technique of tumor removal that causes a less burden to a brain organ such as an optic nerve.

Example 4

[Fabrication of Evaluation Device 1]

Figure 11A:
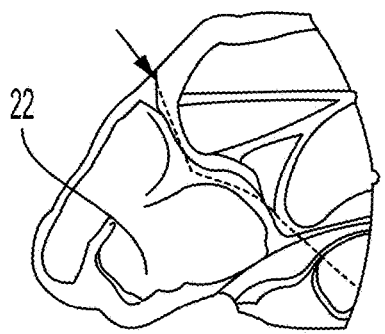
FIG. 11A is a diagram illustrating a place where the distortion sensor of the evaluation device fabricated in Example 4 is formed.

An evaluation device was fabricated by the same process as in Example 1 except that the simulated cranium part 2 to which the simulated dura mater 7 described in Example 2 was attached was used, furthermore, a hollow was formed in the simulated nasal septum 22 of the simulated cranium part 2 as illustrated in FIG. 11A, and the distortion sensor was arranged in the fabricated hollow.

Example 5

[Implementation 2 of Operative Technique Evaluation Method]

Figure 11B:
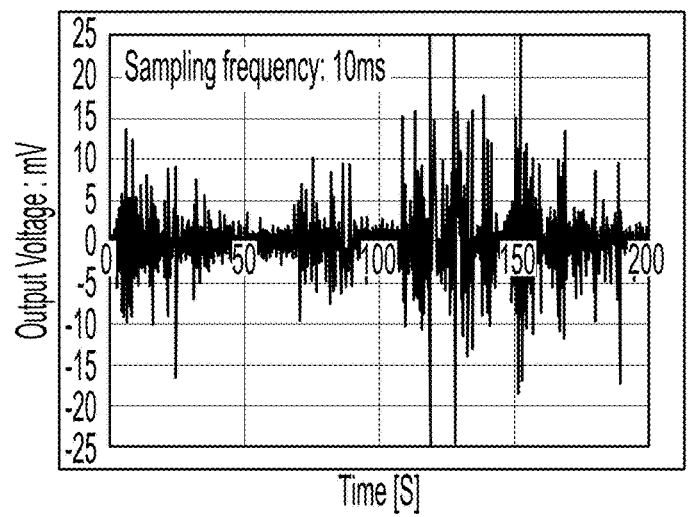
FIG. 11B illustrates a response signal of the distortion sensor obtained by an operative technique evaluation method of Example 5.

Next, the response signal of the distortion sensor was measured when a needle holder (by Fujita Medical Instruments, Co, Ltd., deep site needle holder) used for holding a suture needle for the simulated dura mater 7 was inserted in the simulated nasal cavity 21 after incision of the simulated dura mater 7. FIG. 11B illustrates the response signal obtained in Example 5 in which the peak distant from the base signal near zero on the vertical axis indicates that the needle holder comes into contact with the simulated nasal septum 22, and a larger peak indicates a larger force applied to the distortion sensor. As is clear from FIG. 11B, it was confirmed that it is possible to evaluate external force applied to the cranium part 2 in the endoscopic endonasal surgery by arranging the distortion sensor in the simulated cranium part 2.

As described above, it was confirmed that it is possible to evaluate external force applied to a brain organ and/or a cranial bone in the endoscopic endonasal surgery by using the evaluation model disclosed in the present specification. Since endoscopic endonasal surgery is performed under general anesthesia, it is difficult to obtain evaluation from the patient, such as whether or not it hurts, during the endoscopic endonasal surgery. On the other hand, it is possible to evaluate external force applied to a brain organ and/or a cranial bone when inserting a surgical tool and/or manipulating a surgical tool by using the evaluation model disclosed in the present specification. Therefore, this can achieve a combined effect that the evaluation model disclosed in the present specification can be used for various evaluation such as evaluation of a training apparatus for an inexperienced medical doctor (evaluation of a manual surgical procedure), function evaluation of a surgical apparatus when developing the surgical apparatus that supports endoscopic endonasal surgery, evaluation of a newly designed surgical tool, or the like in addition to evaluation of development of a new operative technique.

INDUSTRIAL APPLICABILITY

According to the evaluation model disclosed in the present specification, it is possible to develop and evaluate an operative technique. Therefore, the evaluation model is useful in the field of medical industries.

LIST OF REFERENCE NUMERALS

1 evaluation model
2 simulated cranium part
3 simulated optic nerve
4 simulated internal carotid artery
5 simulated brain stem
6 simulated tumor
7 simulated dura mater
8 simulated head frame
9 simulated face
21 simulated nasal cavity
22 simulated nasal septum
23 simulated sphenoid bone
24 first simulated cranium part
25 second simulated cranium part
211 superior turbinate
212 middle turbinate
213 inferior turbinate
241 first surface
242 second surface
243 recess
244 first inner surface
245 first outer surface
246 hole
251 third surface
252 cut-off
253 protrusion
254 second inner surface
255 second outer surface

The invention claimed is:

1. An evaluation model for endoscopic endonasal surgery, the evaluation model comprising:
   a simulated head part; and
   a distortion sensor, wherein:
   the simulated head part includes a simulated cranium part,
   the simulated cranium part includes a simulated nasal cavity,
   the simulated cranium part includes a simulated nasal septum, a simulated paranasal sinus, and a simulated cribriform plate,
   the simulated nasal cavity includes a simulated superior turbinate, a simulated middle turbinate, and a simulated inferior turbinate, and
   the distortion sensor is arranged at least one site selected from the group consisting of the simulated superior turbinate, the simulated middle turbinate, the simulated inferior turbinate, the simulated nasal septum, the simulated paranasal sinus and the simulated cribriform plate.

2. The evaluation model according to claim 1, wherein the distortion sensor is arranged at least one site selected from the group consisting of the simulated nasal septum, the simulated paranasal sinus and the simulated cribriform plate.

3. The evaluation model according to claim 1,
   wherein the distortion sensor is arranged in at least one site selected from the group consisting of the simulated superior turbinate, the simulated middle turbinate, and the simulated inferior turbinate.

4. The evaluation model according to claim 1,
   wherein the simulated cranium part includes
   a first simulated cranium part, and
   a second simulated cranium part,
   wherein the first simulated cranium part forms at least a part of a simulated cranial base, and
   wherein the first simulated cranium part and the second simulated cranium part are formed in an attachable and detachable manner.

5. The evaluation model according to claim 4, wherein a simulated dura mater is attached to the first simulated cranium part.

6. The evaluation model according to claim 4,
   wherein fitting parts for fitting the first simulated cranium part and the second simulated cranium part to each other are formed to the first simulated cranium part and the second simulated cranium part, and
   wherein inner surfaces of the first simulated cranium part and the second simulated cranium part form a continuous surface when the first simulated cranium part and the second simulated cranium part are fitted to each other.

7. The evaluation model according to claim 1 further comprising a measuring unit that measures a signal from the distortion sensor.

8. An evaluation model for endoscopic endonasal surgery, the evaluation model comprising:
   a simulated head part,
   a distortion sensor; and
   a simulated tumor, wherein:
   the simulated head part includes a simulated cranium part through which a tumor removal tool passes, the simulated cranium part includes a simulated nasal cavity, the simulated head part includes a simulated brain organ, and the distortion sensor is arranged in the simulated brain organ and the simulated tumor is attached to the simulated brain organ so that the distortion sensor measures external force applied from the tumor removal tool when the simulated tumor is removed by the tumor removal tool.

9. The evaluation model according to claim 8, wherein the simulated brain organ is at least one selected from a simulated optic nerve, a simulated internal carotid artery, a simulated basilar artery, a simulated posterior cerebral artery, and a simulated pituitary gland.

10. The evaluation model according to claim 8, wherein the simulated tumor is attached to at least one site selected from a simulated optic nerve and a simulated pituitary gland of the simulated brain organ.

11. The evaluation model according to claim 8,
wherein the simulated cranium part includes
a first simulated cranium part, and
a second simulated cranium part,
wherein the first simulated cranium part forms at least a part of a simulated cranial base, and
wherein the first simulated cranium part and the second simulated cranium part are formed in an attachable and detachable manner.

12. The evaluation model according to claim 11, wherein a simulated dura mater is attached to the first simulated cranium part.

13. The evaluation model according to claim 11,
wherein fitting parts for fitting the first simulated cranium part and the second simulated cranium part to each other are formed to the first simulated cranium part and the second simulated cranium part, and
wherein inner surfaces of the first simulated cranium part and the second simulated cranium part form a continuous surface when the first simulated cranium part and the second simulated cranium part are fitted to each other.

14. The evaluation model according to claim 8, further comprising a measuring unit that measures a signal from the distortion sensor.

15. A simulated dura mater unit used for an evaluation model for endoscopic endonasal surgery,
wherein the simulated dura mater unit is attached to a first surface of a first simulated cranium part and the first simulated cranium part forms at least a part of a simulated cranial base, and
wherein the first simulated cranium part is configured to form a simulated cranium part of an evaluation model for endoscopic endonasal surgery by being fitted to a second simulated cranium part.

16. An operative technique evaluation method using an evaluation model for endoscopic endonasal surgery,
wherein the evaluation model includes at least
a simulated head part,
a distortion sensor, and
a measuring unit that measures a signal from the distortion sensor,
wherein the simulated head part includes a simulated cranium part, and the simulated cranium part includes a simulated nasal cavity, and
wherein the distortion sensor is arranged in at least a part of the simulated cranium part through which a surgical tool passes, the operative technique evaluation method comprising:
a surgical tool insertion step of inserting the surgical tool in a simulated cranium part via the simulated nasal cavity and/or a surgical tool manipulation step of manipulating the surgical tool inside the simulated cranium part;
a distortion sensor measurement step of measuring the number of times that the surgical tool comes into contact with the distortion sensor arranged in the simulated cranium part and/or force with which the surgical tool comes into contact with the simulated cranium part in the surgical tool insertion step and/or the surgical tool manipulation step; and
an operative technique evaluation step of evaluating the surgical tool insertion step and/or the surgical tool manipulation step from a measurement result of the distortion sensor measurement step.

17. The operative technique evaluation method according to claim 16, wherein:
the simulated cranium part includes a simulated nasal septum, a simulated paranasal sinus, and a simulated cribriform plate,
the simulated nasal cavity includes a simulated superior turbinate, a simulated middle turbinate, and a simulated inferior turbinate, and
the distortion sensor is arranged at least one site selected from the group consisting of the simulated superior turbinate, the simulated middle turbinate, the simulated inferior turbinate, the simulated nasal septum, the simulated paranasal sinus and the simulated cribriform plate.

18. An operative technique evaluation method using an evaluation model for endoscopic endonasal surgery,
wherein the evaluation model includes
a simulated head part,
a distortion sensor,
a measuring unit that measures a signal from the distortion sensor, and
a simulated tumor,
wherein the simulated head part includes
a simulated cranium part, and
a simulated brain organ,
wherein the simulated cranium part includes a simulated nasal cavity,
wherein the distortion sensor is arranged in the simulated brain organ, and
wherein the simulated tumor is attached to the simulated brain organ,
the operative technique evaluation method comprising:
a tumor removal tool approach step of operating a tumor removal tool to approach the simulated tumor via the simulated nasal cavity;
a simulated tumor removal step of removing the simulated tumor by the tumor removal tool;
a distortion sensor measurement step of measuring external force applied to the distortion sensor arranged in the simulated brain organ in the simulated tumor removal step; and
an operative technique evaluation step of evaluating the simulated tumor removal step from a measurement result of the distortion sensor measurement step.

19. The operative technique evaluation method according to claim 18, wherein the simulated brain organ is at least one selected from a simulated optic nerve, a simulated internal carotid artery, a simulated basilar artery, a simulated posterior cerebral artery, and a simulated pituitary gland.

\* \* \* \* \*